United States Patent
Fröhlich et al.

(10) Patent No.: US 10,696,704 B2
(45) Date of Patent: Jun. 30, 2020

(54) METHOD FOR PRODUCING METAL-ORGANIC FRAMEWORKS

(71) Applicants: CHRISTIAN-ALBRECHTS-UNIVERSITÄT ZU KIEL, Kiel (DE); FRAUNHOFER-GESELLSCHAFT ZUR FÖRDERUNG DER ANGEWANDTEN FORSCHUNG E.V., München (DE)

(72) Inventors: Dominik Fröhlich, Freiburg (DE); Albina Holz, Freiburg (DE); Stefan Henninger, Endingen a. K. (DE); Dirk Lenzen, Treia (DE); Helge Reinsch, Kiel (DE); Norbert Stock, Kiel (DE)

(73) Assignees: Christian-Albrechts-Universität Zu Kiel, Kiel (DE); Fraunhofer-Gesellschaft zur Forderrung der Angewandten Forschung E.V., München (DE)

(*) Notice: Subject to any disclaimer, the term of this patent is extended or adjusted under 35 U.S.C. 154(b) by 115 days.

(21) Appl. No.: 15/760,684

(22) PCT Filed: Sep. 19, 2016

(86) PCT No.: PCT/EP2016/072152
§ 371 (c)(1),
(2) Date: Jun. 12, 2018

(87) PCT Pub. No.: WO2017/046417
PCT Pub. Date: Mar. 23, 2017

(65) Prior Publication Data
US 2018/0273568 A1   Sep. 27, 2018

(30) Foreign Application Priority Data
Sep. 17, 2015   (DE) .................. 10 2015 115 738

(51) Int. Cl.
C07F 15/00 (2006.01)
C07F 15/02 (2006.01)
(Continued)

(52) U.S. Cl.
CPC ........... C07F 15/025 (2013.01); B01J 20/226 (2013.01); B01J 20/28064 (2013.01);
(Continued)

(58) Field of Classification Search
None
See application file for complete search history.

(56) References Cited

U.S. PATENT DOCUMENTS

2008/0188677 A1   8/2008   Schubert et al.
2020/0166644       7/2010   Schubert et al.
(Continued)

FOREIGN PATENT DOCUMENTS

DE   102005039623 A1   3/2007
DE   102005039654 A1   3/2007
(Continued)

OTHER PUBLICATIONS

Webpage from: https://medical-dictionary.thefree dictionary.com/derivative, 2019, pp. 1-3.*
(Continued)

*Primary Examiner* — Clinton A Brooks
(74) *Attorney, Agent, or Firm* — Hudak, Shunk & Farine Co. LPA

(57) ABSTRACT

The present invention relates to a method for the preparation of a metal-organic framework structure compound, the metal-organic framework structure compound being prepared such as well as the use of the metal-organic framework structure compound being prepared such as adsorbent.

8 Claims, 3 Drawing Sheets

(51) Int. Cl.
- *B01J 20/22* (2006.01)
- *C07F 5/06* (2006.01)
- *C07C 51/41* (2006.01)
- *B01J 20/28* (2006.01)

(52) U.S. Cl.
CPC ... *B01J 20/28066* (2013.01); *B01J 20/28071* (2013.01); *C07C 51/418* (2013.01); *C07F 5/069* (2013.01)

(56) References Cited

U.S. PATENT DOCUMENTS

| | | |
|---|---|---|
| 2011/0282071 A1 | 11/2011 | Shi |
| 2017/0226040 A1 | 8/2017 | Jeremias et al. |

FOREIGN PATENT DOCUMENTS

| | | |
|---|---|---|
| DE | 102006043648 A1 | 2/2008 |
| DE | 102009027821 A1 | 1/2010 |
| DE | 102014215568 A1 | 2/2016 |
| WO | 2013186542 A1 | 12/2013 |

OTHER PUBLICATIONS

Reinsch, H. et al., Structures, Sorption Characteristics, and Non-linear Optical Properties of a New Series of Highly Stable Aluminum MOFs, Chemistry of Materials 2013, vol. 25, pp. 17-26, ACS Publications.

Cadiau, A. et al., Design of Hydrophilic Metal Organic Framework Water Adsorbents for Heat Reallocation, Advanced Materials, 2015, vol. 27, pp. 4775-4780, Wiley-VCH Verlag GmbH & Co.

\* cited by examiner

METHOD FOR PRODUCING METAL-ORGANIC FRAMEWORKS

FIELD OF THE INVENTION

The present invention relates to a method for the preparation of a metal-organic framework structure compound, the metal-organic framework structure compound being prepared such as well as the use of the metal-organic framework structure compound being prepared such as adsorbent.

BACKGROUND OF THE INVENTION

Heat of adsorption reservoirs provide the possibility of a nearly lossless storage of heat, particularly in the temperature range of up to 250° C., over long periods of time. In particular in connection with the solar thermal heating of buildings in regions of the earth with high seasonal fluctuations of the solarization, i.e. in all regions far away from the equator, a need for such long-term heat reservoirs exists. Here, during the course of the year the highest amount of solar heat from thermal collectors is provided in summer, whereas however the need for thermal heat predominantly exists in winter. In the sense of the development of a sustainable energy supply which is more focused onto regenerative sources of energy the seasonal storage of heat for the heating of buildings is desirable and is a prerequisite for achieving high solar proportions in the solar thermal heating of buildings.

Also, for many other applications the storage of heat in the temperature range of up to ca. 250° C. is an important subject. So e.g. in the case of the decentralized power generation in plants with power-heat coupling (CHP) typically the problem of different temporal need profiles for power and heat arises. For being capable of operating these plants in a power load optimized manner and for being capable of using the generated heat, this heat has to be stored for a certain time, until it is needed. For that, heat reservoirs with high energy density and high efficiency, i.e. low heat losses, are required.

Till today, despite decades of research efforts, heat of adsorption reservoirs have not become accepted on the market. Up to now, primarily, there has been a lack of adsorption materials which provide a large load and heat turnover in the desired temperature range. The zeolites which have often been investigated and used for heat reservoir applications, e.g. zeolites with the structure types LTA and FAU, in particular the commercially available zeolites A, X and Y, typically require for the desorption a driving temperature difference of at least 100° C. between the adsorber and the condenser, thus in the case of a condenser temperature of 35° C. a desorption temperature of at least 135° C. With typical flat plate collectors this temperature cannot be achieved or can only be achieved with very low collector efficiency. Therefore, more expensive evacuated tube collectors or radiation-concentrating collectors are required. With the mentioned zeolites under typical load and unload conditions of a seasonal solar storage system, such as e.g. described in Mittelbach et al., "*Solid sorption thermal energy storage for solar heating Systems*" (TERRASTOCK 2000, Stuttgart, Aug. 28-Sep. 1, 2000), load turnovers of not higher than 0.18 gram water per gram zeolite are achieved. Thus, based on the density of a bed of the zeolite, reservoir energy densities of up to about 150 kWh/m$^3$ can be achieved (A. Hauer, thesis, TU Berlin 2002, "*Beurteilung fester Adsorbentien in offenen Sorptionssystemen für energetische Anwendungen*").

With silica gels comparable energy densities are achieved, but here the main problem is the low usable temperature difference in the case of unloading the reservoir.

Therefore, for the seasonal solar heat storage adsorbents are sought the water adsorption properties of which are between those of typical zeolites and typical silica gels. In particular materials are sought the adsorption isobars of which in the case of a water vapor pressure of about 56 hPa (corresponding to a water reservoir with a temperature of 35° C.) in the temperature range of about 60-110° C. show a load change of at least 0.2 g/g.

Metal-organic frameworks (MOFs) have been developed with respect to a possible use as high temperature hydrogen reservoirs or generally for the sorptive storage of gas (U. Müller, "*Metal-organic frameworks-prospective industrial applications*", J. Mater. Chem. 16 (2006), p. 626-636). Due to the high porosity and surface area they are suitable for diverse further fields of application which are traditionally covered by zeolites, such as for example the heterogeneous catalysis or for gas purification.

MOFs are characterized by a modular design. They consist of inorganic polynuclear complexes (cluster) which serve as connectors in the network. Here, the coordination number and the topology of the connector are determined by the coordinating ligands being directed outwardly. As connecting members (linkers) bi-, tri- and multifunctional ligands are used.

With respect to the technical use, due to the good availability and non-toxicity of the metal, in particularly MOFs on the basis of aluminum as metal clusters hold a lot of promise. However, for a lot of applications the low stability with respect to water and particularly water vapor is a problem.

For example, in the case of the storage of methane in an industrial scale residual moisture cannot be prevented. Also, for the use in heat pumps and refrigerating machines on the basis of the adsorption of refrigerants such as for example water, but also alcohols or natural refrigerants (propane, etc.) a stability with respect to water vapor is a prerequisite. While in the case of the use of water as a refrigerant the stability with respect to water directly arises as a result, also in the case of other refrigerants the stability with respect to water is important, since for example in some process steps the contact with water vapor (atmospheric moisture during the preparation) cannot be avoided. Here, for example the MOF CAU-10-H seems to be very promising, because it exhibits high stability and at the same time good adsorption characteristics.

For the synthesis of MOFs there are different possibilities; most MOFs can be synthesized by solvothermal syntheses. In this case a metal salt and an organic compound are suspended in a solvent or solvent mixture and the reaction mixture is heated in a pressure reactor. This is also the common synthesis for CAU-10-H which can be found in literature (H. Reinsch, M. A. van der Veen, B. Gil, B. Marszalek, T. Verbiest, D. de Vos and N. Stock, *Chemistry of Materials*, 2013, 25, 17-26): As a reaction mixture a suspension of isophthalic acid (1,3-H$_2$BDC) and Al$_2$(SO$_4$)$_3$*18H$_2$O in DMF and water (1:4 parts) is used. The synthesis is conducted in an autoclave with Teflon liners for 12 h at 135° C. It is reported that during the synthesis in a glass reactor an unknown, crystalline minor phase was obtained. In this literature the synthesis of CAU-10-H was conducted in a 37 ml autoclave. It is mentioned that a scale-up in larger autoclaves is conceivable, but no evidence for that is provided.

Especially water-stable MOFs which should be used as sorption material for heat transformation applications are prepared with water at excess pressure which results in the known, technical large-scale problems:
1. Due to the typical reaction temperatures (>100° C.) it is necessary to work under excess pressure and in corresponding vessels (autoclaves).
2. This complicates the reaction control (no view into the vessels) and increases the costs enormously, particularly in the case, when solvothermal syntheses should be used.
3. The use of glass flasks is hardly possible or only in a limited extent.

For MIL-160, a MOF which is isostructural to CAU-10-H, a synthesis without the use of pressure in aqueous solution is known in which furan dicarboxylic acid is reacted with aluminum(III) chloride over a period of time of 24 hours. The purification is achieved by means of centrifugation. On the one hand, the use of aluminum(III) chloride which is corrosive and not water-stable is a disadvantage. The purification by means of centrifugation is time-consuming and effortful with respect to the required equipment.

DE 10 2014 215 568 A1 discloses a method for the preparation of an adsorbent out of metal-organic framework structures. In this case it seems to be possible to prepare the structures at atmospheric pressure. A solvent mixture of DMSO and water is used, wherein a relatively low amount of water and a relatively high amount of DMSO (at least 50% by weight) are used. The target is to achieve with the DMSO a boiling point of higher than 100° C. The water in the reaction mixture only has a minor role, and DMSO is assumed to be decisive for the success of the invention. DMSO has the disadvantage that it forms explosive mixtures with some metal salts which are also used in the synthesis of the MOF. The reaction times are in the order of 24 hours and thus, in comparison to the present invention, are extremely long. The document does not disclose the use of an aqueous solution for the synthesis.

US 2011/0282071 A1 discloses photo-active triazole structures. An example for an aromatic dicarboxylic acid is given. But the synthesis of the aromatic dicarboxylic acid in aqueous solution is not disclosed.

DE 10 2006 043 648 A1 teaches a method for the preparation of MOFs as adsorbent. The synthesis is conducted in an organic solvent having a comparatively high boiling point, e.g. in DMF. The reaction time is in the order of 5 days.

WO 2013/186542 A1 describes a method for the production of MOFs in which benzene dicarboxylates are reacted with metal salts in aqueous solution under ambient pressure. For use in the linkers 2,5-dihydroxyterephthalates (straight linkers) and 1,3,5-benzene tricarboxylic acid salts (branching linkers) are presented as carboxylic acid salts which are reacted with salt mixtures composed of Zn/Na or Ni/Na. References to V-shaped linkers in general or isophthalates and their derivates in particular as well as to aluminum salts cannot be found.

DE 10 2005 039 654 A1 relates to mesoporous MOF compounds. It is described to be decisive that in every case the structural features of at least one nitrogen atom in the heteroaromatic of the linker and of at least three substituents X in the form of carboxyl groups (or their thio derivatives) have to be fulfilled. Otherwise the large specific surface areas and the desired mesoporous structure would not be achieved. Thus, it recommended against the use of aromatic dicarboxylic acids. The synthesis is conducted in organic solvent. The use of water is not recommended. With 4 days the reaction times are very long. Desirable would be a method for the preparation of MOFs which
in comparison to the methods of prior art requires less reaction time,
is harmless with respect to the environment,
does not impose special requirements on the working safety (e.g. danger of explosion),
does not require a considerable amount of equipment (e.g. autoclave) and makes MOFs available in very good quality, particularly with high water stability and large specific surface area.

SUMMARY OF THE INVENTION

Therefore, it was an object of the present invention to provide a synthesis route for CAU-10-H and structurally related MOFs which overcomes the disadvantages of prior art.

DETAILED DESCRIPTION OF THE INVENTION

Figure 1:
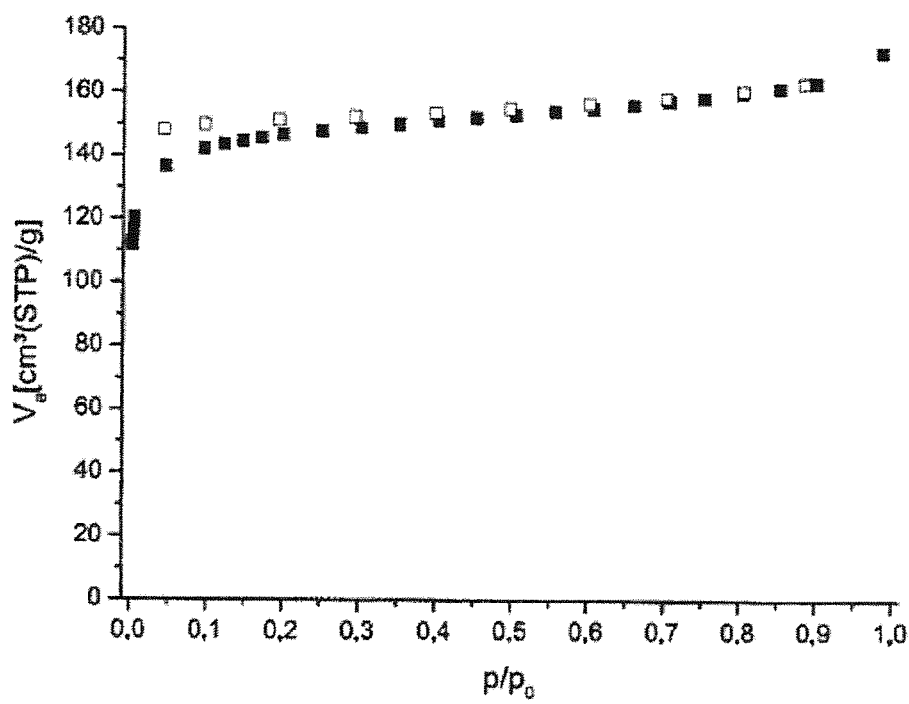
FIG. 1 shows the $N_2$ sorption isotherm, the filled squares describe the adsorption curve and the empty squares describe the desorption curve.

In a first aspect, this object is solved by a method for the preparation of a metal-organic framework structure compound in which at least one metal salt comprising a metal cation which is selected from the group consisting of the transition metals and Al as well as combinations thereof is reacted with a linker compound, characterized in that the reaction is conducted in an aqueous solution at a pressure of 1.5 bar or less. Here, the linker compound is selected from the group consisting of substituted and unsubstituted isophthalates as well as combinations and mixtures thereof.

According to the present invention, isophthalates or derivatives thereof are structures of the general Formula 2.

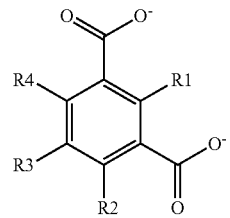

Formula 2

Preferably, the groups R1 to R4 are independently from each other selected from hydrogen, hydroxyl, nitro, amino, methyl, ether and halogenide groups as well as combinations thereof. In preferable embodiments all groups R1 to R4 are hydrogen. In preferable embodiments R3 is selected from amino, nitro, hydroxyl, methyl ether and methyl group.

In embodiments according to the invention the linker compound is selected from isophthalates. According to the present invention, the term "isophthalates" also comprises their derivatives, in particular derivatives comprising a substitution at the position 2, 4, 5 or 6. As suitable substituents hydroxyl, nitro, amino, methyl, ether and halogenide groups as well as combinations thereof can be mentioned.

According to the invention, the reaction is conducted in aqueous solution. Since many aromatic dicarboxylic acids are occasionally characterized by poor solubility in water, it is according to the invention to use the isophthalates. The isophthalates are used in the form of their salts, preferably as sodium, potassium, or ammonium salts.

Preferred metals are Fe, Co, Ni, Zn, Zr, Cu, Cr, Mo, Mn, Al, Pd and combinations thereof, wherein particularly preferred are Al, Fe, Cu, Cr, Zr as well as combinations thereof. In also preferred embodiments the metals are selected from Sc, Ti, V, Cr, Mn, Fe, Co, Ni, Cu, Zn as well as combinations thereof. In particularly preferred embodiments the metal is selected from Al and Fe. Especially in the case of the use of aluminum it is possible to prepare extremely water-stable framework structure compounds. Preferably, the metals are used in the form of their water-soluble salts, particularly the sulfates, nitrates, carbonates, chloride oxides or halogenides. But also other salts each can be used.

According to the present invention, "reacting in aqueous solution" preferably means that substantially no organic solvents are used in the reaction medium. Advantageous aqueous solutions comprise less than 10% by volume, in particular less than 5% by volume, further preferably less than 2% by volume and particularly preferably less than 1% by volume of organic solvent such as DMF. In preferable embodiments the reaction medium does not at all contain any organic solvent. The proportion of water in the aqueous solution is in particular higher than 50% by volume, more preferably at least 70% by volume, particularly higher than 80% by volume and particularly preferably at least 90% by volume or at least 99% by volume.

In special embodiments short-chain alcohols having carbon chain lengths of 1 to 4 carbon atoms, in particular ethanol, can be used in the reaction media of this invention. Their proportion is preferably limited to at most 20% by volume, more preferably at most 10% by volume of the solvent used.

The main issue of the present invention is a new synthesis approach in which, different from prior art, a substantially pressure-less synthesis is conducted. As a further aspect, the present invention preferably comprises the use of solutions of the educts and not of solids and/or suspensions. In particular, in combination with the pressure-less synthesis, this is an advantage. So, as solvent preferably water can be used, and a pressure reactor is not required.

Therefore, in a preferable design of the method according to the present invention the reaction is conducted at a pressure of at least 900 mbar, particularly at least 1 bar. In preferable embodiments the pressure is at most 1.2 bar or at most 1.1 bar. Thus, the reaction can be conducted at atmospheric pressure. From that direct economic advantages follow, when the preparation method is translated into an industrial scale. For example, a continuous production can be realized by removing product being prepared from the process. This can be achieved by filtration. An advantageous design of the method according to the present invention comprises the isolation of the metal-organic framework structure compound being prepared by means of filtration. Isolation of the product by means of filtration can be realized in a continuous method in an easier manner than the isolation by means of centrifugation.

Furthermore, the working-up is substantially easier, since only one step of washing is necessary and no thermal activation for removing, for example, residues of DMF.

As a result, with that the recyclability is significantly increased, and the residues of the synthesis batch can directly be introduced into the clarification plant without any further post-treatment. Thus, also the product is directly free of organic solvent.

In a preferable design of the method according to the present invention the reaction is conducted at a temperature of 80 to 120° C., particularly 90 to 110° C. In one embodiment the reaction temperature is at most 100° C. The reaction is in particular conducted at the boiling point of the reaction medium.

A further technical advantage of the synthesis methodology according to the present invention is that, compared with the poor solubility of the aromatic dicarboxylic acid (isophthalic acid), the aromatic dicarboxylate (isophthalate) can easily be dissolved in water. In particular, when it should be translated into an industrial scale, this results in advantages, since the reaction time is considerably reduced, from 12 h, such as in literature, to, for example, 6 h or 3 h in a flask. As a consequence thereof a higher STY (space-time yield) can be achieved. Therefore, in a preferable design of the method according to the present invention the reaction is conducted over a period of time of 10 hours or less, in particular of 8 hours or less, particularly preferably 6 hours or less.

In a further preferable design of the method according to the present invention the reaction is conducted under irradiation of the aqueous solution with microwaves. But also other methods for heating the reaction vessel which are common for a person skilled in the art are according to the present invention.

In contrast to the synthesis which is known from literature, according to preferred methods according to the present invention the starting materials are aromatic dicarboxylates (isophthalates) and not the aromatic dicarboxylic acid (isophthalic acid) which is characterized by poor solubility in water. Therefore, in the synthesis which is known from literature due to the poor solubility it is necessary to use DMF as a solvent and an increased temperature.

For the method according to the present invention each arbitrary isophthalate can be used. Preferably used are sodium isophthalates, potassium isophthalates, ammonium isophthalates and mixtures thereof.

In principle, for the method according to the present invention, all metal salts being described above can be used. Preferably used are iron and aluminum salts.

In contrast to the synthesis which is known from literature preferably aluminum sulfate in combination with sodium dicarboxylate (e.g. sodium isophthalate) as well as at the same time an inorganic base, particularly sodium hydroxide, calcium hydroxide, potassium hydroxide, ammonia or sodium aluminate in a solution and in a glass vessel instead of a Teflon vessel are used.

In the first instance, the use of Al sulfate is not obvious, since the formation of minor phases, in particular alunite ($KAl_3[(OH)_6(SO_4)_2]$), is considerably increased. For avoiding or for minimizing the formation of these minor phases, preferably potassium hydroxide, sodium hydroxide, calcium hydroxide, ammonia or sodium aluminate is added as a base.

Here, sodium aluminate is used as combined metal source and base which is not taught in literature. Accordingly, in a preferable design of the method according to the present invention as metal salt aluminum sulfate is used. In a further preferable design of the method according to the present invention a base is added to the aqueous solution. Preferably, the base is selected from the group consisting of ammonia, sodium hydroxide, potassium hydroxide, sodium aluminate and potassium aluminate. Particularly preferable is sodium aluminate.

In an alternative preferable design of the method according to the present invention as metal salt iron(III) chloride is used.

The metal-organic framework structure compounds which are prepared by the method according to the present invention being described here are characterized by a particularly high resistance against water. Preferably, the metal-organic framework structure compound has a specific surface area according to BET of 500 m$^2$/g or more.

The metal-organic framework structure compounds produced according to the present invention are used as an adsorbent, wherein the adsorbed material (adsorbate) is preferably water, ethanol, methane, $CO_2$, $H_2$ or a mixture thereof. Preferable is particularly the use of the metal-organic framework structure compounds being described herein for applications such as gas storage, catalysis, dehumidification and heat transformation (e.g. heat pumps, refrigerating machines).

With the method according to the present invention high yields of more than 90%, based on the linker compound, can be achieved. The metal-organic framework structure compounds being prepared with this method have the same or larger surfaces areas, the same or higher capacities with respect to gas sorption and thus the same or better technical properties than metal-organic framework structure compounds being prepared according to a prior art method. In addition, the metal-organic framework structure compounds which have been prepared by reaction in aqueous solution are characterized by the absence of residues of organic solvents.

The present invention will be explained in greater detail by means of the following examples.

EXAMPLES

For the samples to be investigated at the beginning of the ageing process being independent on cycles a starting measurement with nitrogen ($N_2$) at 77 kelvins was conducted on a NOVA 3000e of the company Quantachrome. Via the nitrogen measurement at 77 kelvins information about the change of the pore structure (distribution of the pore radii), pore volumes as well as about the internal surface area (BET) can be gathered. For removing humidity and foreign gases from the samples, before the actual measurement, they were baked out in high vacuum for 24 h at 120° C. Subsequently, the dry weight of the sample was measured by means of an analytical balance of the company Sartorius with the class of accuracy I. Subsequently, complete isotherms in adsorption and desorption were measured and evaluated. The relative pressure range was between p/p0=0.05-0.999 in the case of adsorption and p/p0=0.999-0.1 in the case of desorption. The pore volume was calculated according to the density functional theory (DFT) and according to the model of Dubinin and Astakhov (DA). The internal surface area was calculated according to the model of Brunauer-Emmett-Teller (BET) between p/p0=0.05 and 0.15.

Comparative Example 1

Synthesis:
200 mg of 1,3-isophthalic acid (1,3-$H_2$BDC, 1.20 mmol), dissolved in 1 mL of N,N-dimethyl formamide (DMF), were mixed with 800 mg of $Al_2(SO_4)_3$*18$H_2$O, dissolved in 4 mL of $H_2$O, and treated in a Teflon-lined steel autoclave for 12 hours at 135° C.

Working-Up:
After allowing to cool down to room temperature the product was filtrated and washed with water in an ultrasonic bath. The white solid obtained was dried and subsequently activated at 120° C. in vacuum for 24 hours.

The specific surface area of the product was $S_{BET}$=525 m$^2$/g and the pore volume was 0.27 cm$^3$/g.

Comparative Example 2

Synthesis:
A solution of 0.75 mol (125 g) of isophthalic acid in 600 ml of DMF and 2400 ml of water and 0.72 mmol (483 g) of $Al_2(SO_4)_3$*18$H_2$O were heated in a 5000 ml three-necked flask to 135° C.

In a 5 L flask 483 g (0.72 mol) of $Al_2(SO_4)_3$*18$H_2$O were completely dissolved in 2,4 L of water. To the aluminum sulfate solution 125 g (0.75 mol) of isophthalic acid, dissolved in 600 mL of DMF, were added in portions.

The solution was refluxed under stirring for a period of time of 48 h.

Working-Up:
The solid formed was filtered off with the help of a fluted filter (5-13 μm), resuspended in $H_2O$ and placed in an ultrasonic bath for 30 minutes. This procedure was repeated three times. Subsequently, the white solid was dried for 5 days at 90° C. in the drying oven and for 1 day at 120° C. in the vacuum oven.

Figure 6:
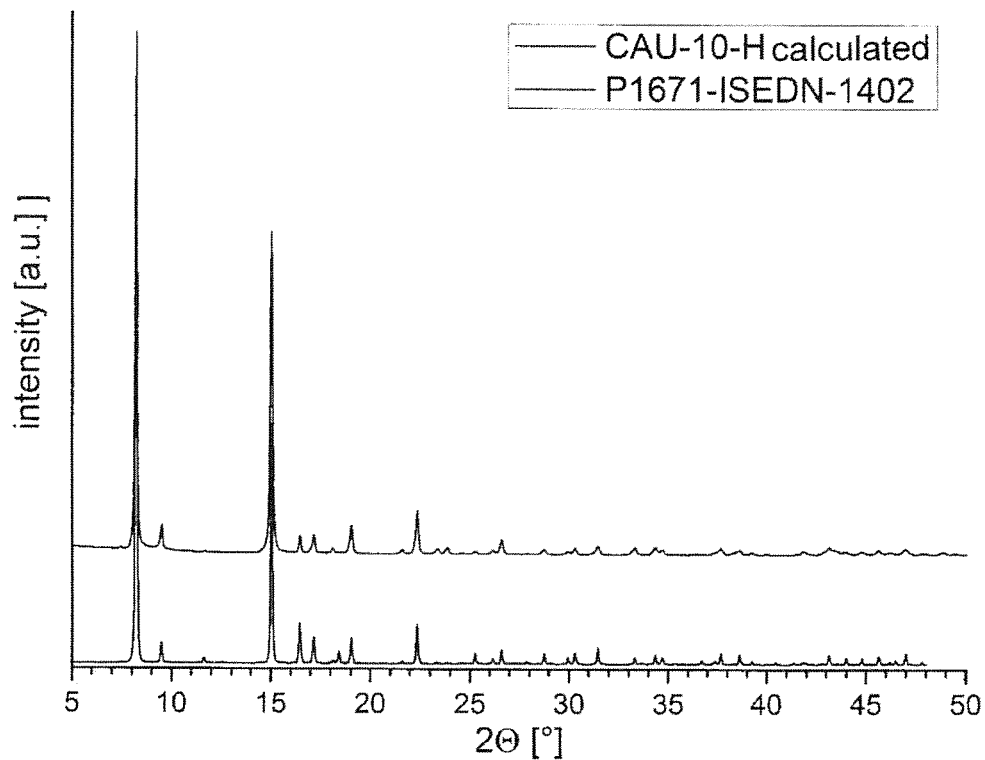
FIG. 6 shows the powder diffractogram of CAU-10-H.

After the purification 156.8 g of a white solid with $S_{BET}$=578 m$^2$/g were obtained. The single crystalline phase was identified by means of X-ray powder diffraction analysis as CAU-10-H. FIG. 6 shows the powder diffractogram of CAU-10-H.

Embodiment Example 1

Synthesis:
5 L of a 0.5 M sodium isophthalate solution were prepared by making up sodium hydroxide (199.99 g; 5 mol) and isophthalic acid (415.33 g; 2.5 mol) in a graduated volumetric flask with $H_2O$ to a volume of 5000 ml. Furthermore, 2 L of a 0.5 M aluminum sulfate*18$H_2$O solution (666.15 g; 1 mol) and 2 L of a 0.5 M sodium aluminate solution (81.79 g; 1 mol), each by making up in a graduated volumetric flask with $H_2O$ to a volume of 2000 mL, were prepared each. For the reaction 2.16 L of sodium isophthalate solution (0.5 M) and 180 mL of ethanol were combined and under stirring 810 mL of aluminum sulfate solution (0.5 M) and 540 mL of sodium aluminate solution (0.5 M) were added. Subsequently, the reaction was conducted for 6 h under reflux and stirring.

Working-Up:
The solid obtained was filtered off, washed with a plenty of water and ethanol and dried over night at 90° C. 207 g (92% yield) of a white powdery solid ($S_{BET}$=580 m$^2$/g) were obtained, and this was identified as CAU-10-H by means of X-ray powder diffraction analysis. The $N_2$ sorption isotherm is shown in FIG. 1; filled squares describe the adsorption curve and empty squares describe the desorption curve.

Embodiment Example 2

Synthesis:

For the synthesis 100 mL of a 0.5 M sodium isophthalate solution were prepared by making up sodium hydroxide (3.99 g, 0.1 mol) and isophthalic acid (8.30 g; 0.05 mol) in a graduated volumetric flask with $H_2O$ to a volume of 100 ml. Furthermore, 100 mL of a 0.5 M aluminum sulfate*$18H_2O$ solution (33.308 g; 0.05 mol) and 100 mL of a 2 M sodium hydroxide solution (7.99 g; 0.2 mol), each by making up in a graduated volumetric flask with $H_2O$ to a volume of 100 mL, were prepared each. For the reaction 127.5 mL of $H_2O$, 7.5 mL of ethanol and 90 mL of sodium isophthalate solution were combined and under stirring 45 mL of aluminum sulfate solution and 22.5 mL of sodium hydroxide solution were added. Subsequently, the reaction was conducted for 6 h under reflux and stirring.

Figure 2:
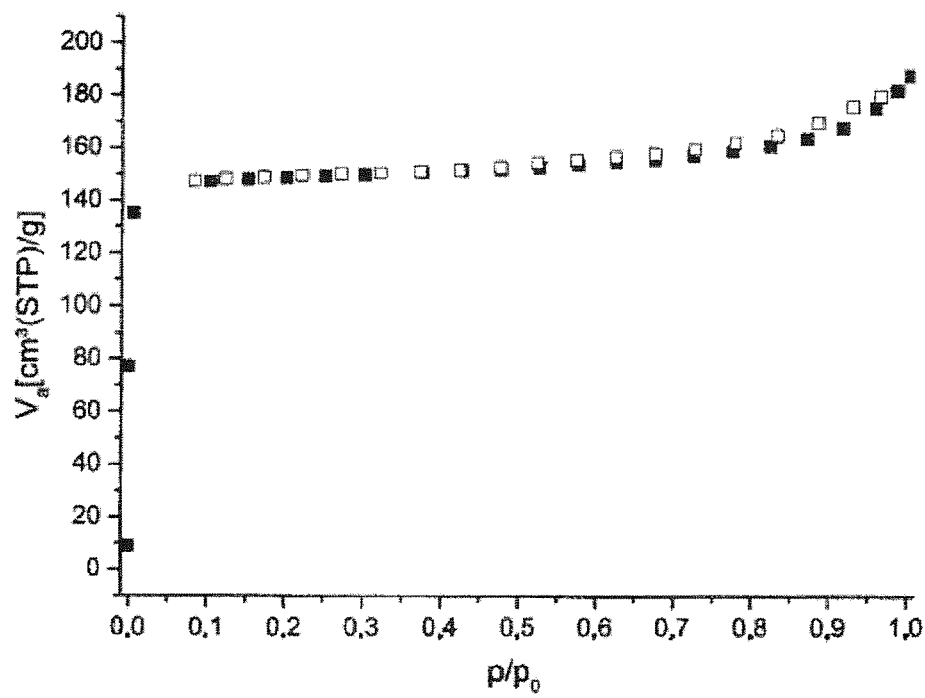
FIG. 2 shows the $N_2$ sorption isotherm, the filled squares describe the adsorption curve and the empty squares describe the desorption curve.

Working-Up:

The solid obtained was filtered off, washed with a plenty of water and ethanol and dried over night at 100° C. A powdery solid ($S_{BET}$=573 $m^2/g$) was obtained which was identified by means of X-ray powder diffraction analysis as CAU-10-H. Furthermore, the reaction product contained a minor phase (sodium alunite, $NaAl_3(OH)_6(SO_4)_2$; #(ICSD)= 44626). The $N_2$ sorption isotherm is shown in FIG. 2; filled squares describe the adsorption curve and empty squares describe the desorption curve.

Embodiment Example 3

Synthesis:

5.25 mL of a 0.5 M sodium isophthalate solution was stirred up with 4.5 mL of water. Under stirring 5.25 mL of a 0.5 M $FeCl_3$ solution were added. Subsequently, the reaction was conducted for 6 h at 95° C. in the microwave under stirring.

Figure 3:
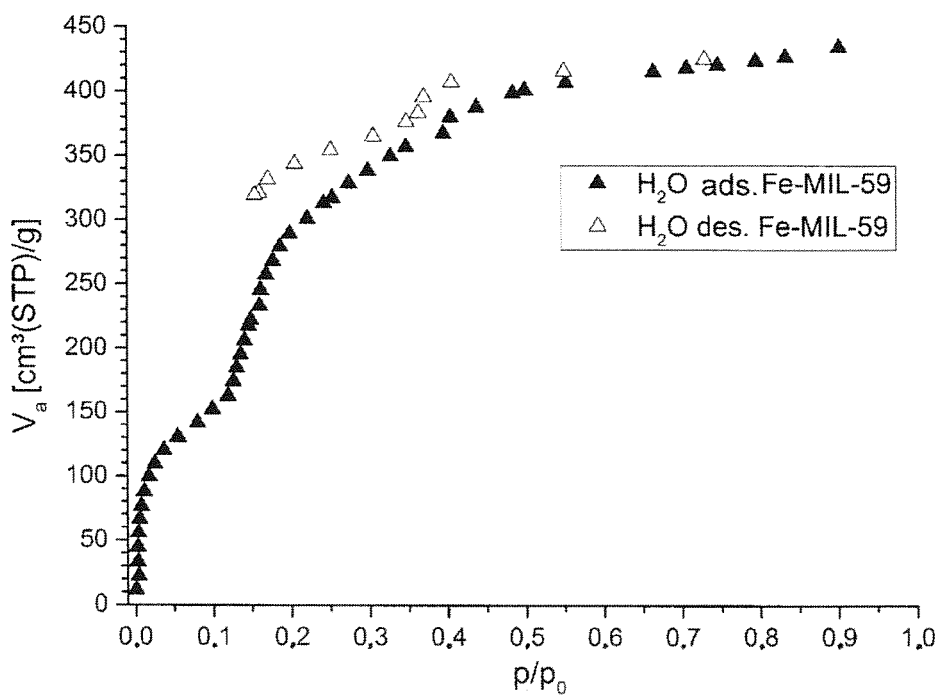
FIG. 3 shows the water sorption isotherm obtained with this substance

Working-Up:

The solid obtained was filtered off, washed with a plenty of water and ethanol and dried over night at 90° C. It was possible to identify it as Fe-MIL-59. FIG. 3 shows the water sorption isotherm obtained with this substance.

Embodiment Example 4

Figure 4:
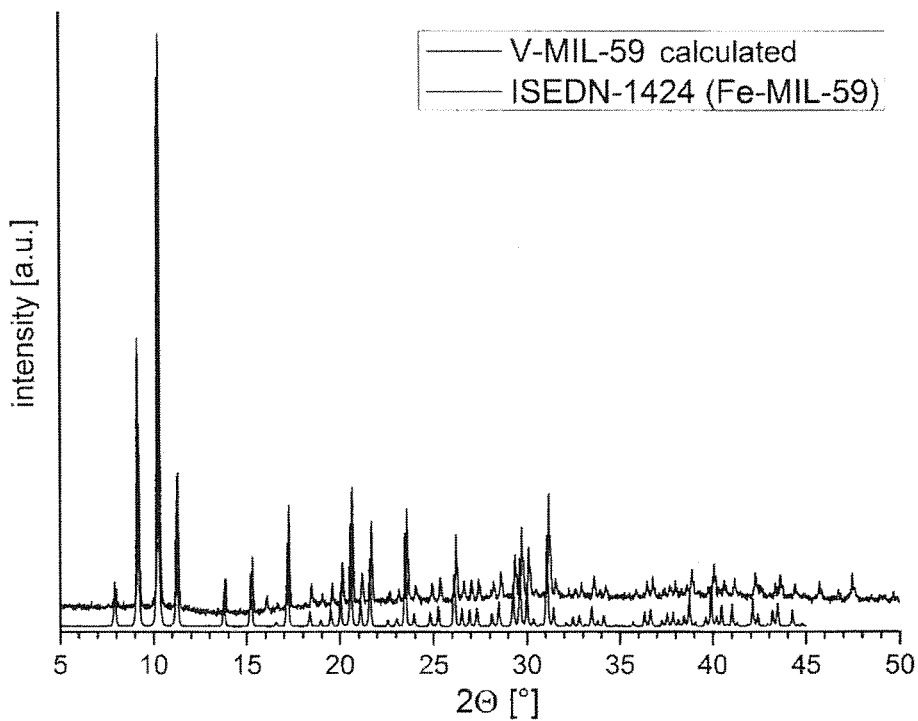
FIG. 4 shows the measured powder diffractogram, as a comparison the diffractogram of vanadium MIL-59 which is isostructural is shown.

For a further synthesis of Fe-MIL-59 100 mL of m-$Na_2$-BDC solution (0.5 M) and 50 mL of water were combined and under stirring 100 mL of $FeCl_3$ solution (0.5 M) were added. The reaction was conducted under vigorous stirring and reflux for 6 hours. The solid obtained was filtered off by means of a very fine filter and the solid was washed thoroughly with water. The product was dried in the drying oven (90° C.) for 3 days. An orange-brown solid was obtained. The yield was 12.55 g (max. 12.8 g, 98%). The powder diffractogram measured is shown in FIG. 4. As a comparison the diffractogram of vanadium MIL-59 which is isostructural is shown.

Comparative Example 3

Figure 5:
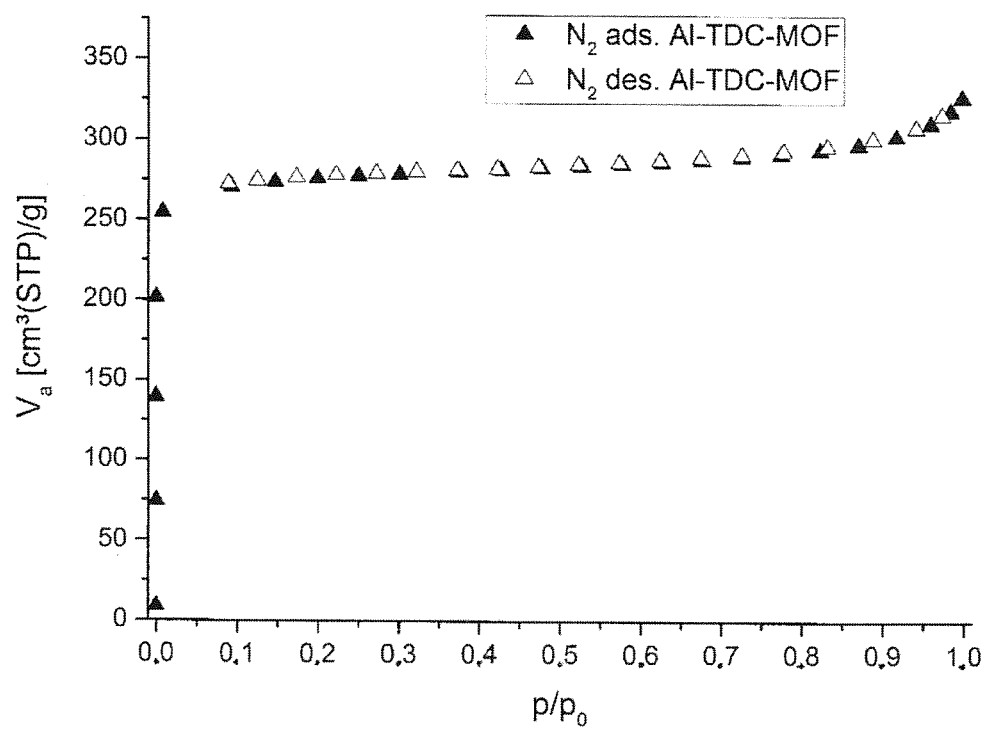
FIG. 5 shows the $N_2$ sorption isotherm.

7.5 mL of $Na_2TDC$ solution (0.5 M) were provided, and under stirring 5.625 mL of $AlCl_3$ solution (0.5 M) and 1.875 mL of $NaAlO_2$ solution (0.5 M) were added. The reaction was conducted for 3 h at 95° C. under stirring in the microwave. The solid obtained was filtrated and washed with water and ethanol. An analysis resulted in a surface area (BET) of 1024 $m^2/g$ and a pore volume=0.4381 $cm^3/g$. FIG. 5 shows the $N_2$ sorption isotherm.

From the comparison of Comparative Example 2 and the embodiment examples 1 and 2 it is obvious that the use of isophthalates in aqueous reaction media substantially reduces the reaction time.

Embodiment Example 3 shows that the reaction does not only work with aluminum as the metal component.

Comparative Example 3 shows that the reaction can analogously be conducted with other aromatic dicarboxylic acids.

What is claimed is:

1. A method for the preparation of a metal-organic framework structure compound comprising the steps of:
    reacting at least one metal salt comprising a metal cation which is selected from the group consisting of the transition metals and Al as well as combinations thereof, with a linker compound, wherein the reaction is conducted at a pressure of less than 1.5 bar in aqueous solution, and wherein the linker compound is an isophthalate.

2. The method according to claim 1, wherein the aqueous solution comprises less than 10% by volume of organic solvents.

3. The method according to claim 1, wherein the reaction is conducted at a temperature of 80 to 120° C.

4. The method according to claim 1, wherein the reaction is conducted over a period of time of 10 hours or less.

5. The method according to claim 1, wherein the linker compounds are structures of the general Formula 2:

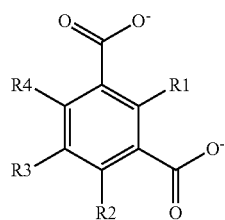

Formula 2 wherein the groups R1 to R4 are independently from each other selected from hydrogen, hydroxyl, nitro, amino, methyl, ether and halogenide groups as well as combinations thereof.

6. The method according to claim 1, wherein the metal salt is selected from the group consisting of iron and aluminum salts.

7. The method according to claim 1, wherein to the aqueous solution a base is added.

8. The method according to claim 1, wherein the reaction is conducted at the boiling point of the reaction medium.

* * * * *